United States Patent [19]
Jenkins et al.

[11] Patent Number: 5,122,471
[45] Date of Patent: Jun. 16, 1992

[54] CLONED GENES CODING FOR AVIAN COCCIDIOSIS ANTIGENS WHICH INDUCE A CELL-MEDIATED IMMUNE RESPONSE

[75] Inventors: Mark C. Jenkins, Bowie; Hyun S. Lillehoj, West Friendship, both of Md.; John B. Dame, Gainesville, Fla.; Harry D. Danforth, Severn; Michael D. Ruff, Bowie, both of Md.

[73] Assignee: The United States of America as represented by the Secretary of Agriculture, Washington, D.C.

[21] Appl. No.: 308,219

[22] Filed: Feb. 9, 1989

Related U.S. Application Data

[63] Continuation-in-part of Ser. No. 155,264, Feb. 12, 1988.

[51] Int. Cl.$^5$ .................. C12N 1/21; C12N 15/00; C12N 15/70; C12P 21/02; C12P 19/34
[52] U.S. Cl. .................. 435/252.3; 435/69.3; 435/91; 435/172.3; 435/320.1; 435/235.1; 435/252.33; 536/27; 530/300; 530/350
[58] Field of Search .................. 435/69.1, 69.8, 91, 435/172.3, 240.2, 252.3, 252.33, 320.1, 235.1, 69.3; 530/300; 536/27; 935/18, 27, 31, 41, 48, 56, 58, 63, 70, 72, 81

[56] References Cited

FOREIGN PATENT DOCUMENTS

| | | |
|---|---|---|
| 135073 | 3/1985 | European Pat. Off. . |
| 223710 | 5/1987 | European Pat. Off. . |
| WO86/00528 | 1/1986 | PCT Int'l Appl. . |
| WO88/06629 | 9/1988 | PCT Int'l Appl. . |

OTHER PUBLICATIONS

Livingston et al. Ann Rev Immunol vol. 5 pp. 477-501 (1987).
Lillehoj Vet Immuno Immunopath vol. 13 pp. 321-330 (1986).
Gubler, V. et al. T . Immunol. vol. 136 pp. 2492-2497 (1986).
H. Wisher, "Identification of the Sporozoite Antigens of *Eimeria tenella*," Molec. Biochem. Parasitol. 21:7-15 (1986).
M. C. Jenkins et al., "Identification of Immunodominant Surface Antigens of *Eimeria acervulina* Sporozoites and Merozoites," Molec. Biochem. Parasitol. 25:155-164 (1987).
M. C. Jenkins et al., "Eimeria acervulina: DNA Cloning and Characterization of Recombinant Sporozoite and Merozoite Antigens," Exp. Parasitol. 66:96-107 (1988).
M. C. Jenkins, "A cDNA Encoding a Merozoite Surface Protein of the Protozoan *Eimeria acervulina* contains Tandem-Repeated Sequences," Nucleic Acids Res. 16(20):9863 (1988).

*Primary Examiner*—Joan Ellis
*Attorney, Agent, or Firm*—M. Howard Silverstein; John D. Fado; Curtis P. Ribando

[57] ABSTRACT

Disclosed are DnA sequences which code for antigenic proteins, methods for identifying such DNA sequences, and antigens coded for by such DNA sequences.

The first step of the method is to provide a multiplicity of DNA sequences. These sequences are then inserted into DNA expression vectors to form recombinant expression vectors. The expression vectors are inserted into suitable hosts to form transformants which express the DNA sequences. The transformants are then contacted with antibodies directed against Eimeria antigens to identify transformants containing DNA sequences which code for Eimeria antigens. These antigens are then produced from the DNA sequences identified as coding for the antigens. The antigens so produced are contacted with white blood cells which effect a cell-mediated immune response, which white blood cells are sensitized to an antigenic Eimeria protein, to thereby identify DNA sequences which code for antigens that induce a cell-mediated immune response to avian coccidiosis.

The DNA sequences of the present invention comprise cloned genes or fragments thereof that code on expression for an antigenic protein that activates white blood cells which effect a cell-mediated immune response, which white blood cells are sensitized to an antigenic Eimeria protein.

8 Claims, No Drawings

CLONED GENES CODING FOR AVIAN COCCIDIOSIS ANTIGENS WHICH INDUCE A CELL-MEDIATED IMMUNE RESPONSE

CROSS-REFERENCE TO RELATED APPLICATION

This is a continuation-in-part of U.S. patent application Ser. No. 07/155,264, field Feb. 12, 1988.

BACKGROUND OF THE INVENTION

1. Field of the Invention

Coccidiosis, an intestinal disorder of poultry, causes an assortment of problems in the infected host. These problems range from poor feed conversion ratios in light infections to acute death in heavier infections. The disease has been estimated to cost U.S. broiler producers $300 million per year, due in part to unrealized weight gains, loss of skin pigmentation, and poor feed utilization, and in part to the cost of anticoccidial drugs.

Coccidiosis is caused by protozoans belonging to the genus Eimeria. The members of this genus have a complicated life cycle which consists of both asexual and sexual stages. The cycle is initiated when birds ingest sporulated oocysts (generally associated with fecal material). These oocysts contain invasive asexual sporozoites which are released into the bird's digestive tract. The sporozoites invade epithelial cells and develop into multinucleate structures called schizonts. Each schizont matures and releases numerous invasive asexual structures, known as merozoites, into the bird's digestive tract, where they in turn invade other epithelial cells. The sexual stage of the coccidiosis life cycle is initiated when merozoites differentiate into gametocytes. The developing asexual and/or sexual stages produce the pathological digestive tract lesions characteristic of coccidiosis. Gametocytes then fuse and the fertilization products, called oocysts, are released in the feces. The formation of oocysts completes the parasite's life cycle.

Infection by protozoans of the genus Eimeria can be alleviated, and even prevented, by the administration of anticoccidial agents. However, drug-resistant strains arise at a frequent rate and the cost of development of anticoccidials is quite high. Chickens can be vaccinated against the disease by infection with live attenuated strains of Eimeria or with nonliving parasite material. However, there is an appreciable disease effect using the former approach and a prohibitive amount of material would be required to make the latter useful on a large-scale basis. Furthermore, protection with the latter is far from complete. An alternative solution would be to produce, by genetic engineering, the protective antigens of Eimeria parasites. Once developed, these immunogens could be produced in a prokaryotic or even eukaryotic culture system in an unlimited supply and used to vaccinate chickens against subsequent disease.

2. Description of the Prior Art

Immune responses are mediated by two different effector mechanisms. One mechanism, which involves the production of antibodies by lymphoid tissue, is termed "humoral immunity." The other, which involves the activation of white blood cells such as T-lymphocytes previously sensitized to the immunogen, is termed "cell-mediated immunity." See *Immunology: Basic Processes*, 2nd ed., page 12, J. Bellanti (1985).

PCT Application Publication No. WO 86/00528 to Anderson et al., titled "Cloned Gene and Method for Making and Using the Same," discloses cloned genes which code for antigenic proteins of Eimeria species. The procedure taught by this application for screening transformed cells to identify these DNA sequences involves the use of polyvalent chicken antiserum obtained from chickens previously infected with *Eimeria tenella*. See Id. at 9, 41-43, and 44. Chicken antiserum, however, reflects only the humoral immune response of the bird to the antigen to which the bird has been exposed, and does not reflect the bird's cell-mediated immune response. Accordingly, the Anderson patent teaches how to obtain DNA sequences which code for the production of antigens which evoke a humoral immune response. While an important contribution to the art, Anderson does not address whether these same antigens evoke a cell-mediated immune response, and—if not—how such antigens might be obtained. Nor does it address the relative contribution of the cell-mediated immune response and the humoral immune response to the integrated immune response of birds to avian coccidiosis.

Accordingly, an object of the present invention is to provide a means for producing DNA sequences which code for antigens which evoke a cell-mediated immune response to avian coccidiosis.

An additional important object of the present invention is to provide a means for identifying DNA sequences which code for antigens which evoke a cell-mediated immune response to avian coccidiosis and which may not otherwise be identified by prior art procedures.

A further object of the present invention is to provide cloned genes which code for Eimeria sporozoite or merozoite cell-surface antigens, particularly *Eimeria acervulina* cell-surface antigens.

A still further object of the present invention is to provide transformed host cells which produce antigens which evoke a cell-mediated immune response to avian coccidiosis.

Still further objects of the present invention are to provide methods and vaccines useful for protecting birds against avian coccidiosis.

Other objects and advantages of this invention will become readily apparent from the ensuing description.

SUMMARY OF THE INVENTION

The present invention, in a first respect, involves a method for obtaining desired DNA sequences. The method involves, initially, providing a multiplicity of Eimeria DNA sequences (ultimately provided as either a genomic DNA or complementary DNA library). These sequences are then inserted into DNA expression vectors to form recombinant expression vectors. Next, the recombinant expression vectors are inserted into suitable hosts to form transformants which express the DNA sequences. These transformants are then screened with (i.e., contacted with) antibodies which are directed against Eimeria cell-surface antigens to identify transformants containing DNA sequences which code for Eimeria cell-surface antigens. After this, Eimeria cell-surface antigens are produced from the DNA sequences identified as coding for such antigens. These Eimeria cell-surface antigens are then contacted with white blood cells that have been sensitized to an antigenic Eimeria protein (specifically, white blood cells which effect a bird's cell-mediated immune response) to thereby identify DNA sequences which code for antigens that induce a cell-mediated immune response to avian coccidiosis.

It has unexpectedly been found that, by following the foregoing procedure, DNA sequences which code for antigenic proteins useful as vaccines for avian coccidiosis can be obtained which could not be obtained by prior sequence identification processes. DNA sequences provided by the foregoing procedure which are not provided by prior art procedures are identified by contacting the Eimeria cell-surface antigens produced by the procedure described above with immune sera taken from an Eimeria infected bird. Those antigens not recognized by the immune sera are coded for by DNA sequences which would not have been identified by prior art procedures.

A second aspect of the present invention is the products which may be produced by the foregoing procedures. These products are DNA sequences which comprise a cloned gene or fragment thereof that code for antigens which activate white blood cells. The white blood cells, which have been sensitized to an antigenic Eimeria protein, effect a cell-mediated immune response. The antigens are preferably directed against Eimeria cell-surface antigens, such as Eimeria sporozoite or Eimeria merozoite cell-surface antigens. One group of DNA sequences of the present invention code for antigenic proteins not recognized by immune sera taken from Eimeria-infected birds.

Recombinant expression vectors are also disclosed herein. These vectors comprise an expression vector having a promoter and a DNA sequence as described above inserted in the vector downstream of the promoter and operatively associated therewith. Transformed cells disclosed herein, useful for making antigens, comprise a host cell and a recombinant DNA expression vector as described above contained within the host cell. The expression vector promoter is selected so as to be operable in the host cell.

A further aspect of the present invention is the antigens produced by the transformed host cells, which antigens are discussed in part above. These antigens comprise proteins or fragments thereof that activate white blood cells, which white blood cells effect a cell-mediated immune response, and which white blood cells are sensitized to an antigenic Eimeria protein.

Methods and vaccines useful for protecting birds against infection by avian coccidiosis are also disclosed herein. The method comprises administering to a bird an antigen as described above in an amount effective to immunize the bird against avian coccidiosis. The vaccines are comprised of such antigens, in an amount effective to immunize a bird against avian coccidiosis, in combination with a pharmaceutically acceptable carrier. The term "immunize," as used herein, means any level of protection which is of some benefit in a population of birds, whether in the form of decreased mortality, decreased lesion scores, improved feed conversion ratios, or the reduction of any other detrimental effect of avian coccidiosis, regardless of whether the protection is partial or complete.

DEFINITIONS

The following terms are employed herein:

Cloning. The selection and propagation of (a) genetic material from a single individual, (b) a vector containing one gene or gene fragment, or (c) a single organism containing one such gene or gene fragment.

Cloning Vector. A plasmid, virus, retrovirus, bacteriophage or nucleic acid sequence which is able to replicate in a host cell, characterized by one or a small number of restriction endonuclease recognition sites at which the sequence may be cut in a predetermined fashion, and which contains a marker suitable for use in the identification of transformed cells, e.g., tetracycline resistance or ampicillin resistance. A cloning vector may or may not possess the features necessary for it to operate as an expression vector.

Codon. A DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine ("Leu"), TAG, TAA, and TGA are translational stop signals, and ATG is a translational start signal.

DNA Sequence. A linear series of nucleotides connected one to the other by phosphodiester bonds between the 3' and 5' carbons of adjacent pentoses.

Expression. The process undergone by a structural gene to produce a polypeptide. Expression requires both transcription of DNA and translation of RNA.

Expression Vector. A plasmid, virus, retrovirus, bacteriophage, or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence.

Fusion Protein. A protein produced when two heterologous genes or fragments thereof coding for two different proteins not found fused together in nature are fused together in an expression vector. For the fusion protein to correspond to the separate proteins, the separate DNA sequences must be fused together in correct translational reading frame.

Genome. The entire DNA of an organism. It includes, among other things, the structural genes encoding for the polypeptides of the substance, as well as operator, promotor and ribosome binding and interaction sequences including sequences such as the Shine-Dalgarno sequences.

Heterologous DNA. A DNA sequence inserted within or connected to another DNA sequence which codes for polypeptides not coded for in nature by the DNA sequence to which it is joined.

Nucleotide. A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine ("T"). The four RNA bases are A, G, C, and uracil ("U").

Phage or Bacteriophage. Bacterial virus many of which include DNA sequences encapsidated in a protein envelope or coat ("capsid"). In a unicellular organism a phage may be introduced by a process called transfection.

Plasmid. A nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance ("Tet$^R$") transforms a cell previously sensitive to tetracycline into one which is resistant to it. A cell transformed by a plasmid is called a "transformant."

Polypeptide. A linear series of amino acids connected one to the other by peptide bonds between the alpha-amino and carboxy groups of adjacent amino acids.

Promoter. A DNA sequence within a larger DNA sequence defining a site to which RNA polymerase may bind and initiate transcription.

Reading Frame. The grouping of codons during translation of mRNA into amino acid sequences. During translation the proper reading frame must be maintained. For example, the DNA sequence GCTGGTTGTAAG may be translated via mRNA into three reading frames, each of which affords a different amino acid sequence:

```
GCT GGT TGT AAG - Ala—Gly—Cys—Lys
C CTG GTT GTA AG - Leu—Val—Val
GC TGG TTG TAA A - Trp—Leu-(STOP)
```

Recombinant DNA Molecule. A hybrid DNA sequence comprising at least two DNA sequences, the first sequence not normally being found together in nature with the second.

Ribosomal Binding Site. A nucleotide sequence of mRNA, coded for by a DNA sequence, to which ribosomes bind so that translation may be initiated. A ribosomal binding site is required for efficient translation to occur. The DNA sequence coding for a ribosomal binding site is positioned on a larger DNA sequence downstream of a promoter and upstream from a translational start sequence. Shine-Dalgarno sequences are prokaryotic ribosomal binding sites.

Start Codon. Also called the initiation codon, is the first mRNA triplet to be translated during protein or peptide synthesis and immediately precedes the structural gene being translated. The start codon is usually AUG, but may sometimes also be GUG.

Structural Gene. A DNA sequence which encodes through its template or messenger RNA ("mRNA") a sequence of amino acids characteristic of a specific polypeptide that is an integral constituent of a cellular organelle (such as a cell membrane).

Transcription. The process of producing mRNA from a structural gene.

Translation. The process of producing a polypeptide from mRNA.

DEPOSIT OF BIOLOGICAL MATERIAL

*Escherichia coli* strain MA16, containing the MA16 clone described herein (Example 20), and *Escherichia coli* strain cSZ1, containing the cSZ-1 clone described herein (Example 10), have been deposited under the provisions of the Budapest Treaty in the Agricultural Research Culture Collection (NRRL) in Peoria, Ill., and have been assigned Accession Nos. NRRL B-18867 and NRRL 18868, respectively.

DETAILED DESCRIPTION OF THE INVENTION

In practicing the present invention, any protozoan species in the genus Eimeria may be employed. These include *Eimeria acervulina, E. mivati, E. mitis, E. prae-cox, E. hagani, E. necatrix, E. maxima, E. brunetti,* and *E. tenella*. These protozoa are known and available to those skilled in the art, as avian coccidiosis is found on poultry farms throughout the world. See, e.g., M. Wisher, Molec. Biochem. Parasitol. 21 (7): 7-15 (1986); P. Murray et al., European Patent Application Publication No. 0223710; R. Schenkel et al., European Patent Application Serial No. 0135073. Particularly preferred for practicing the present invention is *E. acervulina*.

The present invention may be practiced with any bird susceptible to avian coccidiosis, including chickens, turkeys, ducks, geese, quail, partridge, and pheasant. A particularly preferred bird with which to practice the present invention is the chicken.

A multiplicity of DNA sequences obtained from an Eimeria species for use in practicing the present invention may be generated by conventional techniques. One approach is to digest the genomic DNA of an Eimeria species, with the ultimate goal being the preparation of a genomic DNA library. See generally R. Old and S. Primrose, *Principles of Gene Manipulation*, 102–109, 3rd ed. (1985). A more preferable approach is to isolate mRNA from an Eimeria species and generate cDNA sequences therefrom, with the ultimate goal being the preparation of a cDNA library. See generally R. Old and S. Primrose, supra, at 109–111; T. Maniatis, E. Fritsch, and J. Sambrook, *Molecular Cloning: A Laboratory Manual*, 187–246 (1982). DNA sequences in a cDNA library do not contain introns, as these have been removed by the splicing of the mRNA from which the cDNA sequences are prepared. If the DNA sequences are to be expressed in a bacterial host, they should preferably be cDNA sequences, as eukaryotic introns are not spliced out by bacteria.

A variety of vector-host combinations may be employed in practicing the present invention. Host cells may be either prokaryotic or eukaryotic cells, and, when the host cells are bacterial cells, they may be either gram-negative or gram-positive bacteria. Useful hosts include *Escherichia coli* (including, for example, *E. coli* X1776, *E. coli* X2282, *E. coli* HB101, and *E. coli* MRC1), species of Salmonella (including, for example, *S. typhimurium, S. enteriditis,* and *S. dublin*) species of Pseudomonas (including, for example, *P. aeruginosa* and *P. putida*), *Bacillus subtilis*, yeasts and other fungi (for example, *Saccharomyces cerevisiae*), plant cells such as plant cells in culture (including, for example, both angiosperms and gymnosperms) and animal cells such as animal cells in culture.

Vectors used in practicing the present invention are selected to be operable as cloning vectors or expression vectors in the selected host cell. The vectors may, for example, be bacteriophage, plasmids, viruses, or hybrids thereof. Vectors useful in *E. coli* include plasmids (for example, pSC101, ColE1, RSF2124, pBR322, pBR324, pBR325, pAT153, pUC-6 and pUC-8), bacteriophage-γ, cosmids, phasmids, and filamentous coliphages. Salmonella species may be transformed, for example, with plasmids such as pJC217, pBRD001, and pBRD026. Vectors useful in gram-negative bacteria generally include plasmids of incompatibility groups P, Q, or W, which have broad host ranges (for example, Sa, RP4, and RSF1010), and Transposons such as TnT. *Bacillus subtilis*, a gram-positive bacteria, can be transformed with *S. aureus* plasmids (for example, pC194, pE194, pSA0501, pUB110, and pT127). Yeast host vectors include yeast integrating plasmids (such as pYeLeu 10), yeast episomal plasmids (such as pJDB219 and pJDB248), yeast replicating plasmids (which contain an autonomously replicating sequence, or "ars," derived from a yeast chromosome), and yeast centromere plasmids (which contain centromeres functional in yeast). Plant cell vectors include Geminiviruses, Caulimoviruses (such as CaMV, CERV, DaMV, FMV, MMV, CVBV AND ThMV), and *Agrobacterium tumefaciens* containing Ti plasmids. Mammalian cell vectors include viruses (such as SV40), retroviruses, and adenoviruses.

Within each specific vector various sites may be selected fro insertion of the isolated DNA sequence. These sites are usually designated by the restriction enzyme or endonuclease that cuts them. For example, in pBR322 the Pst I site is located in the gene for penicillinase between the nucleotide triplets that code for amino acids 181 and 182 of the penicillinase protein.

The particular site chosen for insertion of the selected DNA fragment into the vector to form a recombinant vector is determined by a variety of factors. These include size and structure of the polypeptide to be expressed, susceptibility of the desired polypeptide to enzymatic degradation by the host cell components and contamination by its proteins, expression characteristics such as the location of start and stop codons, and other factors recognized by those of skill in the art. None of these factors alone absolutely controls the choice of insertion site for a particular polypeptide. Rather, the site chosen reflects a balance of these factors, and not all sites may be equally effective for a given protein.

Eimeria DNA sequences may be inserted into the desired vector by known techniques. If, however, the vector is to serve as an expression vector, the vector should have a promoter, and the DNA sequence should be inserted in the vector downstream of the promoter and operationally associated therewith. The vector should be selected so as to have a promoter operable in the host cell into which the vector is to be inserted (that is, the promoter should be recognized by the RNA polymerase of the host cell). In addition, the vector should have a region which codes for a ribosome binding site positioned between the promoter and the site at which the DNA sequence is inserted so as to be operatively associated with the Eimeria DNA sequence once inserted (preferably, in correct translational reading frame therewith). The vector should be selected to provide a region which codes for a ribosomal binding site recognized by the ribosomes of the host cell into which the vector is to be inserted. For example, if the host cell is to be a prokaryotic cell such as *E. coli*, then the region which codes for a ribosomal binding site may code for a Shine-Dalgarno sequence.

A preferred method for carrying out the present invention is with vectors which produce a fusion protein. Such vectors include, in order from upstream to downstream, a promoter, a region which codes for a ribosomal binding site, a translational start codon, a sequence which codes for a first protein or fragment thereof immediately following the translational start codon, and a site at which the second Eimeria DNA sequence is inserted. The Eimeria DNA sequence (which codes for a protein or fragment thereof different from the first DNA sequence, e.g., β-galactosidase) is inserted in the vector so that it is spliced directly to the first sequence and is in correct translational reading frame therewith. The first and second DNA sequence thereby together code for a fusion protein.

In the present invention, transformed host cells are screened with antibodies (monoclonal or polyclonal) directed against Eimeria cell-surface antigens prior to the step of screening for white blood cell activation.

Prior art procedures employ immune sera taken from Eimeria infected birds. Such sera is not directed specifically to cell-surface antigens. In the present invention, polyclonal antibodies taken from an animal which has been administered denatured Eimeria cell-surface antigens are employed. Alternatively, monoclonal antibodies directed against specific Eimeria cell-surface antigens may be employed.

One unique development disclosed herein involves the use of monoclonal antibodies directed to the Eimeria refractile body. Through the use of such antibodies, DNA sequences which code for a refractile body protein or fragment thereof are identified. These DNA sequences may also be employed in practicing the present invention.

Antibodies directed against Eimeria cell-surface antigens may be obtained by procedures known in the art. See, e.g., J. G. Timmins, et al., Gene 39:89 (1985); H. Danforth and P. Augustine, Poult. Sci. 62:2145 (1983); see generally G. Kohler and C. Milstein, Nature 256:495 (1975). These antibodies may be of any origin, but are preferably rabbit or murine (mouse or rat) antibodies. They may be of any class of immunoglobulin, including IgG, IgA, IgD, IgE, and IgM. Preferred is IgG, such as IgG1, IgG2, IgG3, and IgG4.

For screening against white blood cells, the antigens coded for by the DNA sequence of interest may be produced by any conventional means. It may be expressed from the same vector and host cell in which it was originally cloned, transferred to a different host for expression, or transferred to a different vector and host for expression. The antigenic expression product is then extracted from the host cell culture and used in the white blood cell screening step.

White blood cells useful for practicing the present invention include any white blood cells which effect a cell-mediated, as opposed to humoral, immune response. Such cells include, for example, granulocytes (such as basophils and mast cells, eosinophils, and neutrophils), T-lymphocytes, macrophages, K cells, and NK cells. The white blood cells should be white blood cells sensitized to an Eimeria antigen. Particularly preferred for practicing the present invention are T-lymphocytes. Procedures for determining whether such cells are activated by an antigen are either known to those skilled in the art or will be apparent to those skilled in the art through the present disclosure, and include both in vitro and in vivo tests. For example, the antigen could be topically applied to an Eimeria sensitized subject and the region to which the antigen was applied examined for a wheal and flare reaction. Suitable subjects for such a test would include rabbits, rats, and mice. Alternatively, the antigen could be injected subcutaneously into the wattle of an Eimeria sensitized chicken and the chicken's wattle examined for swelling. The most quantifiable procedure, and therefore most preferable, is to incubate white blood cells taken from an Eimeria sensitized bird in an aqueous solution containing the antigen. See also H. Lillehoj, Immune Response During Coccidiosis in SC and FP Chickens I. In vitro assessment of T cell proliferation to stage specific parasite antigens. Vet. Immunol. Immunopathol. 13:321 (1986); See also, M. Beaven et al., J. Pharm. Exp. Ther. 224:620 (1983); M. Beaven et al., Clin. Chim. Acta 37:91

(1972). Preferably, the white blood cells are obtained (removed from) a bird during the bird's second exposure to Eimeria. At such time the bird's white blood cells, which have previously been sensitized, are increasing in number.

Numerous issued U.S. patents are available which disclose information useful to those skilled in the art in practicing the present invention. U.S. Pat. No. 4,710,463 to Murray discloses recombinant DNA expression vectors incorporating DNA sequences coding for Hepatitis B virus antigens. U.S. Pat. No. 4,601,980 to Goeddel and Heyneker discloses the expression of a gene coding for human growth hormone in a pBR322/E. coli system. U.S. Pat. No. 4,590,163 to Helinski and Ditta discloses RK2 plasmids useful for gene cloning in gram-negative bacteria such as E. coli. U.S. Pat. No. 4,237,224 to Cohen and Boyer discloses methods for producing recombinant DNA expression vectors. U.S. Pat. No. 4,332,897 to Nakano et al. discloses lambdoid bacteriophage vectors useful for transforming E. coli. U.S. Pat. No. 4,332,901 to Goldstein discloses a P4 derivative bacteriophage cloning vector. U.S. Pat. No. 4,704,362 to Itakura and Riggs and U.S. Pat. No. 4,356,270 to Itakura disclose recombinant plasmid vectors useful for transforming microbial hosts. U.S. Pat. No. 4,273,875 to Manis discloses a plasmid designated pUC6 useful as a cloning vector for transforming microbial hosts. U.S. Pat. No. 4,349,629 to Carey et al. discloses plasmid vectors employing the trp bacterial promoter useful as recombinant DNA expression vectors. U.S. Pat. No. 4,362,817 to Reusser discloses the plasmid pUC1060, which contains a tet gene promoter, useful as an expression vector. U.S. Pat. No. 4,599,308 to Hamer et al. discloses SV40 expression vectors which can be introduced into eukaryotic cells. U.S. Pat. Nos. 4,693,976 to Schilperoort et al., U.S. Pat. No. 4,536,475 to Anderson, and 4,459,355 to Cello and Olsen all concern the transformation of plant cells with the Ti plasmid of Agrobacterium tumefaciens. The disclosures of all U.S. patent references cited herein are to be incorporated herein by reference.

In the examples below, three specific DNA sequences coding for Eimeria cell surface antigens are disclosed. Clone MA1 is disclosed in Table I, clone cMZ-8 is disclosed in Table II, and clone MC17 is disclosed in Table III. The sequences are shown in their 5' to 3' orientation. Those skilled in the art can make numerous uses of this information. First, working from the same Eimeria acervulina starting materials, they can reisolate the same sequences. Second, they can generate oligonucleotide probes homologous to the sequences shown in the tables and isolate DNA sequences which hybridize to the probes. Such probes are preferably at least 16, and more preferably at least 20, nucleotides in length. Still greater binding selectivity is achieved with probes 30 nucleotides or more in length, but the advantages of probes having lengths much greater than this tend to be offset by the disadvantage of the decreased yields of longer probes which can be synthesized. Third, in view of the known degeneracy of the genetic code (more than one codon codes for the same amino acid), they can produce different DNA sequences which code on expression for the same polypeptides coded for on expression by any of the foregoing DNA sequences.

The antigens of the present invention may be administered by any convenient route, such as subcutaneously, intraperitoneally, or intramuscularly, in the presence of a physiologically acceptable diluent. The antigens may be administered in a single dose or in a plurality of doses. The antigens of the present invention may be administered, if desired, in combination with vaccine stabilizers and vaccine adjuvants. Typical stabilizers are, for example, sucrose, an alkali metal hydrogen phosphate salt, glutamate, serum albumin, gelatin, or casein. The stabilizer may be any one or more of the foregoing. The adjuvant may be, for example, alum or a composition containing a vegetable oil, isomannide monooleate and aluminum monostearate. The antigens of the present invention may be stored under refrigeration or in frozen or lyophilized form.

Antigens may be administered to birds via biological routes. A transformed host cell which expresses a DNA sequence coding for an antigen may be administered to a bird so that the host cell expresses the antigen in the bird. For example, a transformed Salmonella host may be orally administered to the bird. Alternatively, the antigen may be incorporated into a vector capable of transforming avian cells (for example, a retrovirus) and that vector administered to the subject bird so that the birds own cells serve as host cells for the vector, express the antigen, and present the antigen to the subject. All of these procedures are procedures for making and administering antigens of the present invention to birds to protect these birds from avian coccidiosis.

The following examples are provided to more completely explain the present invention. They are for illustrative purposes only, and are not to be taken as limiting thereof.

EXAMPLE 1

Extraction of RNA from Sporozoites

A mixture of sporulated and unsporulated Eimeria acervulina oocysts ($2.2 \times 10^9$ total) were homogenized in a Potter-Elvheim grinder in the presence of DNA/RNA extraction buffer (4M guanidine isothiocyanate, 0.1M B-mercaptoethanol, 10 mM ethylenediamine tetraacetic acid (EDTA), 5 mM sodium citrate, 0.5% sodium sarcosine). The homogenate was diluted into 1.6 volumes cesium trifluoracetate and centrifuged at 45,000 rpm for 16 hrs at 20° C. The RNA band was removed by syringe needle puncture of the centrifuge tube and was diluted in 2 volumes 100% ethanol and stored for 15 min at −70° C. The precipitating RNA was pelleted by centrifugation at 10,000 rpm for 30 min at 4° C. The RNA pellet was washed twice with 70% ethanol and collected by centrifugation. The RNA pellet was dried in vacuo and then dissolved in $H_2O$. The RNA solution was extracted twice with a 1:1 solution of phenol-chloroform, twice with chloroform, and then precipitated overnight with 0.1 volume 3M sodium acetate and 2.5 volume ethanol at −20° C. The RNA was collected by centrifugation, dried in vacuo, and dissolved in $H_2O$.

EXAMPLE 2

Extraction of RNA from Merozoites

Merozoites of E. acervulina ($2.9 \times 10^9$ total) were obtained from infected chickens and purified as described in Jenkins and Dame, Molec. Biochem. Parasitol. 25:155 (1987). The merozoites were disrupted by pipetting in the presence of DNA/RNA extraction buffer. The isolation of RNA thereafter was identical to the procedure described for sporozoite RNA isolation (Section 1).

EXAMPLE 3

Selection of Subpopulations of RNA Having Poly A Tails

RNA from sporozoites and merozoites were passed through an oligo-dT cellulose column (Pharmacia) to enrich for poly A+ RNA (i.e., mRNA). Once bound, the poly A+ RNA was eluded from the column with distilled H₂O, collected, and precipitated with ethanol and sodium acetate. The mRNA was pelleted by centrifugation, washed with 80% ethanol, centrifuged once again, dried in vacuo, and dissolved in H₂O.

EXAMPLE 4

Preparation of Sporozoite and Merozoite cDNA Libraries From the Respective Sporozoite and Merozoite mRNA

A. Preparation of recombinant bacteriophage γ DNA cDNA was generated from poly A+ RNA of *E. acervulina* sporozoites and merozoites using established techniques. See Gubler and Hoffman, Gene 25:263–269 (1983). In brief, first strand cDNA synthesis was accomplished by priming with oligo dT in the presence of RNAsin, the appropriate dNTPs, and Moloney Murine Leukemia Virus (MMLV) reverse transcriptase. cDNA synthesis was halted after 1 hr at 37° C. with EDTA and the cDNA-RNA mixture was phenol-chloroform extracted and precipitated with ethanol and sodium acetate, centrifuged, dried in vacuo, and resuspended in H₂O. Second strand synthesis was carried out in the presence of dNTPs and RNase H by DNA polymerase I. After a 1-hr incubation at 15° C. followed by a 1 hr incubation at 22° C., the reaction was halted and the double-stranded cDNA was phenol-chloroform extracted, precipitated with ethanol and ammonium acetate, collected by centrifugation, dried in vacuo, and resuspended in 50 mM Tris, pH 7.6, 1 mM EDTA, 5 mM DTT. The cDNA was methylated with s-adenosyl methionine by EcoRI methylase and the cDNA ends polished with T4 DNA polymerase I. After phenol-chloroform extractions, ethanol precipitation, centrifugation, and drying in vacuo, the methylated cDNA was tailed with EcoRI linkers using T4 DNA ligase and RNA ligase. The cDNA was then digested with EcoRI restriction enzyme for 1.5 hrs at 37° C. to produce EcoRI compatible ends, stopped with EDTA, phenol-chloroform extracted, ethanol precipitated, collected by centrifugation, dried in vacuo, resuspended in 10 mM Tris, pH 7.5, 0.1 mM EDTA, 0.4 M NaCl, and passed over a NACS column (Bethesda Research Laboratories). The cDNA was eluted with high salt buffer (2M NaCl in TE), ethanol precipitated, collected by centrifugation, dried in vacuo, and resuspended in TE. The cDNA was ligated to γgt11 DNA containing compatible EcoRI ends using T4 DNA ligase at 4° C. for 16 hrs.

B. Packaging of Recombinant Bacteriophage-γ DNA into Virions and Transfection of *E. coli* Y1090

Recombinant sporozoite cDNA- and merozoite cDNA-bacteriophage DNA was packaged into intact virions using a Packagene extract following the procedures described by the manufacturer (Promega Biotech). After packaging, an aliquot of the recombinant bacteriophage was used to transfect *Escherichia coil* strain Y1090 cells. After infection, the cells were plated on Luria broth (LB) agar plates in LB agarose containing 0.2% X-gal, 4 mM IPTG, and 75 μg/ml amplicillin. Using this technique, greater than 95% of the bacteriophage were observed to be recombinants (i.e., contained cDNA inserts) as judged by the percentage of white plaques of the total plaques obtained. The sporozoite and merozoite cDNA libraries were estimated to contain $4.1 \times 10^6$ and $2.4 \times 10^6$ clones, respectively.

EXAMPLE 5

Identification of Recombinant Phages by Screening *E. coli* With Immune Sera from Rabbits Administered *E. acervulina* Sporozoite or Merozoite Membrane Fractions

A. Preparation of Immune Sera

In order to screen the cDNA bacteriophage libraries, immune sera were generated by immunizing rabbits with denatured membrane preparations of *E. acervulina* sporozoites or merozoites. Individual rabbits were immunized intramuscularly with either denatured sporozoite or denatured merozoite membranes emulsified in Complete Freund's adjuvant and boosted with an identical dose in Incomplete Freund's Adjuvant (1 μg membrane protein) two times further at 1-wk intervals. Immune sera were collected when antisporozoite and antimerozoite ELISA titers reached a plateau and were processed using standard methods. See, e.g., Shiigi and Slomick, 111 *Selected Methods in Cellular Immunology*, Mishell and Shiigi, eds., pages 295–305 (1980). Prior to screening the bacteriophage libraries, immune sera were absorbed with *E. coli* Y1090 cellular extract to remove anti-*E. coli* antibodies.

B. Immunoscreening of Recombinant Bacteriophages

Aliquots (approximately $10^5$ clones) of the SZ and MZ bacteriophage libraries were used to transfect *E. coli* Y1090 and plated as described in Section 4B. The plates containing developing phage plaques were overlaid with nitrocellulose disks which had been soaked in 10 mM IPTG and were incubated at 37° C. for 4 hrs to induce production of the galactosidase fusion protein. The nitrocellulose disks, impregnated with the *E. coli* proteins containing the recombinant fusion protein, were removed, treated with phosphate-buffered saline (PBS) containing 0.05% Tween 20 and 1% BSA for 30 min at room temperature to block nonspecific antibody (Ab) binding. The filter disks were then incubated overnight with a $10^{-2}$ dilution of absorbed rabbit antisporozoite membrane sera or antimerozoite membrane sera. The Ab binding was developed by subsequent treatment with biotinylated antirabbit (or antimouse) IgG followed by avidin-peroxidase. Substrate (0.5 mg/ml 4-chloro-1-napthol and 0.1% H₂O₂) was added and positive bacteriophage cDNA plaques were identified and removed from the respective culture plates with a pasteur pipet into phage dilution buffer. Fifty-five positive sporozoite clones and 44 positive merozoite clones were identified.

EXAMPLE 6

Subcloning of Selected Bacteriophages in *E. coli* Y1090

Once identified and removed from the respective culture plates each of the positive bacterlophage identified in Example 1 above were subcloned by several rounds of plating, screening, and isolation similar to the steps described in Section 5B. This procedure was repeated until 100% of the plaques from each individual clone produced a positive signal upon immunoscreening.

EXAMPLE 7

Transfer of Selected Bacteriophages into E. coli Y1089 and Production of Fusion Proteins Therefrom The titer of each clonal bacteriophage preparation prepared in Example 6 above was determined by infecting E. coli Y1090 and plating on LB agar containing ampicillin. Individual aliquots of an overnight culture of E. coli Y1089 were infected at a M.O.I. equal to 10 with separate bacteriophage cDNA clones and grown at 32 C. Individual colonies were picked into microtiter plates in a grid design and replica plated onto two LB agar-ampicillin culture plates. One inoculated plate was grown at 32° C., the other grown at 42° C. Colonies growing at the lower temperature, but not at the higher, indicative of a lysogenic state, were isolated and grown in bulk culture in LB broth containing ampicillin at 32° C. When the $O.D._{550}$ of the bulk culture reached 0.4–0.5 the temperature was shifted to 42° C. and held at that level for 20 min to induce the lytic cycle. After a temperature shift to 37° C., the culture was induced with 2 mM IPTG for 1.5 hrs. The E. coli were then harvested by centrifugation at 2500 rpm for 15 min at 25° C. and the cell pellet was resuspended in a volume of 0.01M Tris, pH 7.4, 5 mM $MgCl_2$, 10 μg/ml leupeptin and chymostatin, and 0.5 mM TPCK and TLCK. The E. coli were lysed by freeze-thawing and disrupted further by sonication for 20 sec. on ice. The homogenate was treated with 10 μg/ml DNase and RNase for 10 min on ice and then centrifuged at 10,000 g for 15 min at 4° C. and the resulting supernatant stored at −20° C. for further analysis.

EXAMPLE 8

Purification of Fusion Proteins

The β-galactosidase fusion proteins produced by the procedures described in Example 7 above were purified by high-performance liquid chromatography (HPLC) using a GF 250 molecular sieve column (DuPont) after dilution in 6M urea (due to the insoluble nature of the recombinant antigens). One-minute fractions (0.5 ml/fraction) were collected and assayed for β-galactosidase fusion protein by ELISA. The partially purified recombinant antigens were dialyzed against several 1—l changes of DMEM.

EXAMPLE 9

Screening of Purified Fusion Proteins with T Cells Obtained from E. acervulina Infected Chickens Immune T lymphocytes were collected from inbred strains of chickens (Hy-Line International Production Center) that had been inoculated per os at 4–8 wks of age with $10^5$ sporulated oocysts of E. acervulina and a second time with the same dose 5 wks later. T cell proliferation assays were carried out 5–10 days after the second inoculation as described by Lillehoj, Vet. Immunol. Immunopath. 13: 321 (1986). In brief, splenic lymphocytes ($3-4 \times 10^6$) enriched for T cells by passage over nylon wool, see Julius et al., Euro. J. Immunol. 3: 645-650 (1973), were cocultured with different concentrations of sporozoites ($1-2 \times 10^6$) or HPLC-purified recombinant antigens prepared in Example 8 above (50–100 ng) in microtiter plates. Concanavalin A (Sigma Chemical Co.) as a positive control and identical fractions of γgt11 lysogen extracts purified by HPLC as a negative control were included in each assay. In all assays, mitomycin C treated normal spleen cells ($3.4 \times 10^4$) were used as antigen presenting cells. Cultures were incubated for 3 days at 41° C. in a humidified atmosphere of 5% $CO^2$ in air. The cultures were pulsed 18 hrs before harvesting with 1 μCi of $^3$H-deoxythymidine ($^3$H-TdR, New England Nuclear). The cultures were harvested using a PHD cell harvester (Cambridge Technology, Inc.) and the amounts of $^3$H-TdR uptake quantified on a B-scintillation counter (Beckman Instruments, Inc.).

Of the 5–10 fusion proteins screened, those designated cSZ-1 and cMZ-8 appeared to be of most interest. There was a measurable increase in the level of $^3$H-thymidine incorporation by immune SC T lymphocytes cocultured with cSZ-1 compared to γgt11 controls. This increased response was similar when normal SC spleen cells or LSCT-RP9 cells were used as the source of APC. There was a much greater level of activation of immune SC T lymphocytes by recombinant cMZ-8 antigen at the highest concentration tested. These responses to cSZ-1 and cMZ-8 appear to be relevant to infection since T cells from uninfected, normal controls exhibited negligible stimulation in the presence of either of the recombinant E. acervulina antigens (e.g., $^3$H-TdR incorporation by normal T cells in the presence of recombinant antigens was less than 20% of that by immune T cells).

EXAMPLE 10

Subcloning of Recombinant cDNA Into pUC-8, Transformation of E. coli JM83 Therewith, and Production of Cloned Genes Therefrom CSZ-1 and cMZ-8 were subcloned into pUC-8 to facilitate determining the molecular organization and DNA sequence thereof. High titer bacteriophage preparations were produced, see, Maniatis et al. (1982), and concentrated by centrifugation over CsCl. Bacteriophage DNA was prepared [Maniatis et al., (1982)], digested with EcoRI to release the cDNA insert, the products separated by agarose electrophoresis, and the cDNA insert isolated by electroelution and passage through a NACS column. The cDNA insert was ligated to pUC-8 plasmid DNA which contained compatible EcoRI ends. Recombinant plasmid DNA was used to transform competent JM83 cells using standard procedures. See, e.g., Hanahan, J. Molec. Biol. 166: 557 (1983). Plasmid DNA was generated as described [Maniatis et al., (1982)] and the cDNA insert isolated as outlined above.

EXAMPLE 11

Characterization of the cSZ-1 Antigen

For labeling and hybridization studies, plasmid DNA was digested with EcoRI, electrophoresed on IMP agarose (FMC), and the insert DNA band was excised, placed in electrophoresis buffer in dialysis bags and electroeluted for 2 hrs at 100 volts. The dialysate was extracted twice with phenol, once with phenol-chloroform, and once with chloroform and the insert DNA precipitated with ethanol and sodium acetate. The insert DNA was labeled with 10 μCi of $^{32}$p-alpha dCTP (3000 μCi/mMole, New England Nuclear) by nick translation, Rigby et al., J. Molec. Biol. 113: 237 (1977), using DNase I and DNA polymerase (BRL). Labeled DNA was separated from $^{32}$P-dCTP by passage over a 18 cm $\times$ 0.4 cm Sephadex G-50 column (Pharmacia). *E. acervulina* sporozoite and merozoite DNA was purified as described by Dame and McCutchan, Molec. Biochem. Parasitol. 8: 263 (1983), except that 2 μg/ml ethidium bromide and CsTFA instead of CsCl was used in the centrifugation step. The purified DNA (2 μg) was digested with 30 units of either EcoRI, EcoRV, HindIII, or Dra I restriction enzymes (BRL), electrophoresed in agarose (FMC) and transferred to Biodyne membrane (Pall) using Southern blotting procedures. See Southern, J. Molec. Biol. 98: 503 (1975). After transfer, the DNA-blotted Biodyne paper was baked in vacuo at 80° C. for 2 hrs, prehybridized with 0.5M NaCl, 0.05M NaCitrate, pH 7.0 (6X SSC), 0.2% tetra-sodium pyrophosphate, 0.2% sodium dodecylsulfate (SDS), and 50 μg/ml heparin (Sigma) for 6 hrs at 65° C., and hybridized with $10^6$ cpm of $^{32}$P-labeled probe for 16–20 hrs at 65° C. The blots were washed three times with 0.1X SSC, 0.1% SDS at 65° C. for 30 min per wash and once with 0.05X SSC, 0.1% SDS for an additional 30 min at 65° C. The blots were air dried and overlaid with photographic film (Kodak XAR) to visualize the hybridization patterns.

The lysogens were induced with 2 mM IPTG as described by Young and Davis, Genetic Engineering, Volume 7, J. Setlow and A. Hollander, eds., (1985), were harvested by centrifugation (2500 g), and lysed by freeze-thawing and sonication for 20 sec in 0.01M Tris-HCl, pH 7.4, 0.005M $MgCl_2$, and 0.5 μg/ml chymostatin, leupeptin, 0.005M TLCK, TPCK. After sonication, the *E. coli* homogenates containing the fusion protein were treated with 10 μg/ml RNase and DNase to destroy nucleic acids and were centrifuged at 7500 g for 15 min to pellet unbroken cells and large particulate material. Protein concentrations were determined using the BCA technique (Pierce Chemical Co.). The β-galactosidase fusion proteins were purified by immunoaffinity chromatography on an anti-β-galactosidase column following the techniques described by the manufacturer (Promega Biotech).

Aliquots of *E. coli* homogenates containing the fusion protein were diluted in 2X sample buffer (20% glycerol, 10% 2-mercaptoethanol, 4.6% SDS, 0.125M Tris, pH 6.8) and run on a 4% stacking/7.5% resolving SDS-polyacrylamide gel as described by Laemmeli Nature 227: 680 (1976). The SDS-page separated proteins were transferred to nitrocellulose paper (Schleicher and Schuell) as described by Towbin et al., Proc. Nat. Acad. Sci. U.S.A. 76(9): 4350 (1980). After Western blotting, the nitrocellulose paper was treated with 0.01M $NaH_2PO_4$ pH 7.3, 0.01M NaCl (PBS) containing 0.05% Tween 20 and 5% nonfat dry milk (NFDM). Immune sera ($10^{-2}$ dilution) and monoclonal antibodies reactive with β-galactosidase ($2 \times 10^{-4}$ dilution) were diluted in PBS-Tween 20-NFDM and used to probe Western blots as described by Jenkins and Dame, Molec. Biochem. Parasitol. 25: 155 (1987). Polyclonal antibodies specific for the β-galactosidase fusion proteins were purified from immune rabbit sera raised to *E. acervulina* sporozoite and merozoite membrane extracts using described procedures. Ozaki et al., J. Immunol. Methods 89: 213 (1986). *E. acervulina* sporozoites ($10^8$) and merozoites ($10^8$–$10^{10}$) were $^{125}$I-surface labeled using the Iodogen method. See, e.g., Markwell, Biochem. 17(22): 4807 (1980). Whole cell protein extracts were prepared, separated by SDS-PAGE, transblotted to nitrocellulose paper and probed with immune sera using methods similar to those described above.

The foregoing techniques revealed that the cDNA insert cloned in cSZ-1 was 1580 bp in length and contains an internal EcoRI site which divides the sequence into a 960 bp (upper) fragment and a 620 bp (lower) fragment. Each of the two fragments were subcloned into pUC8 and γgt11. The respective β-galactosidase fusion proteins in γgt11 (upper and lower) were expressed and immunoscreened with rabbit anti-*E. acervulina* sporozoite serum. Identical fusion proteins were obtained from cSZ-1 and cSZ-1U (upper), thus, immunoreactive parasite protein was associated with the larger 960 bp fragment. Clones of the smaller 620 bp fragment were not immunoreactive. The 960 bp sequence from subclone pcSZ-1U in pUC8 was cleaved from the vector by EcoRI digestion, separated by agarose electrophoresis, electroeluted, and labeled with $^{32}$P-dCTP by nick translation for use as a probe.

The cSZ-1U probe hybridized to either one or two major bands on Southern blots of *E. acervulina* DNA digested with EcoRI, EcoRV, HindIII, or DraI. Although only data from EcoRI digested sporozoite and merozoite DNA is presented, hybridization was to the same bands in DNA from both stages of the parasite for each restriction enzyme. A single hybridization band was observed for both HindIII- and DraI-digested *E. acervulina* DNA while two bands of similar intensities were seen for EcoRI and EcoRV digested genomic DNA. Except for the two bands found in EcoRI digested genomic DNA, these findings can be explained by restriction mapping data. The pcSZ-1U insert DNA contains a single EcoRV site and no DraI or HindIII sites. It is unclear why pcSZ-1U hybridizes to two EcoRI fragments of genomic DNA since no EcoRI sites are present in the insert DNA. It is possible that the gene exists in more than one copy within the genome or that the genomic sequence giving rise to the mRNA from which the 960 bp cDNA was prepared is interrupted with an intron which contains EcoRI and EcoRV sites.

Lysogens of *E. coli* Y1089 containing the cSZ-1 insert were treated with IPTG to induce production of the cSZ-1 β-galactosidase fusion protein. Homogenates containing the fusion protein were prepared, separated by SDS-PAGE, transblotted to nitrocellulose paper, and probed with mouse McAb specific for β-galactosidase and with rabbit sera raised to sporozoite membrane extracts. The cSZ-1 fusion protein appears to be 130 kDa in size. The size of the fusion proteins produced by this clone indicated that only about 30% of the total 960 bp insert encodes parasite protein. Similar to other β-galactosidase fusion proteins, Schoner et al., Biotechnology 3: 151–154 (1985), cSZ-1 forms insoluble aggregates. About 50% of the reactive p130 antigen was present in the pellet after sonication and the 7500 g centrifugation. Transblots of the cSZ-1 fusion protein lysate were also probed with sera from chickens immune to *E. acervulina* as a result of a previous infection with this protozoan. There did not appear to be any detectable recognition of the cSZ-1 fusion protein by the immune chicken sera.

Antibodies reactive with the cSZ-1 fusion protein were absorbed and purified from rabbit antisporozoite membrane sera and used to probe Western blots of $^{125}$I-labeled *E. acervulina* sporozoite proteins. Two protein bands, one at Mr 240, the other at Mr 160, were recognized as antigens homologous for the cSZ-1 fusion protein. Although detectable $^{125}$I-labeling is evident, neither the p240 nor the p160 antigen appears to be a major sporozoite surface protein. Immunoblotting of $^{125}$I-labeled sporozoite proteins with sera from mice immunized with purified cSZ-1 confirmed that the fusion protein is homologous to a region of the Mr240 and Mr160 antigens.

EXAMPLE 12

Characterization of the cMZ-8 Antigen

Clone cMZ-8 was characterized using the same procedures as described in Example 11 above. Clone cMZ-8 contains an insert size of 800 bp which was released by EcoRI digestion, purified from agarose gels by electroelution, and subcloned into pUC8 plasmid giving rise to clone pcMZ-8. Gel-purified pcMZ-8 insert DNA was labeled by nick translation and used to probe Southern blots of restriction enzyme-digested *E. acervulina* sporozoite and merozoite DNA. A single fragment of *E. acervulina* genomic DNA (sporozoite or merozoite) bound probe for each restriction enzyme combination (EcoRI, EcoRV, HindIII, DraI) suggesting that only a single copy of the sequence may be present in the genome. Similar to the pcSZ-1 hybridization results, there was no significant difference in the banding patterns between sporozoite and merozoite DNA for each restriction digest.

Fusion proteins of cMZ-8 were prepared as lysates of the respective *E. coli* Y1089 lysogen, separated by SDS-PAGE, and transblotted to nitrocellulose paper as above. The blots were probed with anti-$\beta$-galactosidase McAb and with rabbit sera raised to *E. acervulina* merozoite membrane extracts. The cMZ-8 fusion protein appears to be 145-150 kDa in size. The parasite encoded portion of this 150 kDa $\beta$-galactosidase fusion protein is estimated to be about 35 kDa which is similar to the estimated size based on the length of the cDNA insert (800 bp). Similar to the cSZ-1 fusion protein, at least 50% of the cMZ-8 protein is present as insoluble aggregates. Antibodies to the cMZ-8 protein were purified from rabbit antisera specific for merozoite membranes and used to probe Western blots of $^{125}$I-labeled merozoite proteins. The respective parasite protein appears to be 230-250 kDa with a considerable number of breakdown products and/or cross-reactive antigens between Mr 75-230 kDa. The p230-250 antigen is a surface protein as indicated by $^{125}$I-labeling. These results were confirmed by probing Western blots of $^{125}$I-labeled merozoite proteins with sera from mice that had been immunized with $\beta$-galactosidase column-purified cMZ-8 protein.

EXAMPLE 13

Immunization of Chickens with cSZ-1 and cMZ-8

Separate groups of 1-wk-old Sexsal chickens were immunized intramuscularly with varying doses of either cSZ-1 or cMZ-8 recombinant antigens or the appropriate controls, boosted with an identical dose 1 wk later, and challenged the following week with $10^3$ sporulated oocysts of *Eimeria acervulina*. After 5 days the chickens were sacrificed and examined for signs of disease (e.g., intestinal lesion score). Although no differences were found for body weight gains, there was a significant ($P<0.05$) decrease in the lesion score from cSZ-1 and cMZ-8 immunized birds compared to that observed in the control groups.

EXAMPLE 14

Immunization of Chickens with cSZ-1 and cMZ-8 and with Reduced Lipopolysaccharide In the previous vaccine trial it was noted that administration of the recombinant sporozoite (cSZ-1) and merozoite (cMZ-8) antigens and $\gamma$gt11 control *E. coli* extracts had a depressive effect on weight gains compared to unimmunized controls. To determine if endotoxin (i.e., lipopolysaccharide, LPS) was responsible for this effect we removed a substantial amount ($>50\%$) of the LPS by treating the antigen extracts with Polymixin B agarose. Again, separate groups of 1-wk-old Sexsal chickens were immunized with varying doses of either LPS containing or LPS-depleted cSZ-1 or cMZ-8 recombinant antigens or the appropriate controls. The chickens were boosted with identical doses two times thereafter, one and 2 wks post-initial immunization, and challenged the following week with $10^3$ oocysts of *Eimeria acervulina*. After 5 days the chickens were sacrificed and examined for signs of disease. While removal of LPS did improve weight gains prior to oocyst challenge there was no significant difference in body weight gains between groups of chickens that were immunized with the recombinant antigens or those receiving the $\gamma$gt11 control. However, lesion scores in the chickens that were immunized with either recombinant antigen from which LPS had been removed were significantly lower than lesion scores from either the $\gamma$gt11 controls or recombinant antigen preparations which contained LPS.

EXAMPLE 15

Identification of Recombinant Phages by Screening *E. coli* With Monoclonal Antibodies Specific for the Sporozoite Stage of *E. acervulina*

To obtain monoclonal antibodies (McAb) reactive with either stage of the parasite, BALB/C mice were immunized intravenously with $10^6$ *E. acervulina* sporozoites or merozoites and boosted with an identical dose 2 wks later. Spleen cells from immunized mice were obtained 3 d after the last immunization and fused with P$_3$X myeloma cells in the presence of polyethylene glycol using described procedures. See Zola and Brooks, Techniques for the Production and Characterization of Monoclonal Hybridoma Antibodies, in *Hybridoma Antibodies: Techniques and Applications*, pages 1-57, J. G. R. Hurrell, ed. (1978). In brief overview, the hybridomas were grown in Dulbecco's minimal essential medium (DMEM) containing fetal bovine serum, hypoxanthine, aminopterin, and thymidine in flat bottom microtiter plates (Costar) and stored at 37° in a 5% CO incubator. Supernatants from wells containing proliferating hybridoma colonies were assayed for antibodies reactive with dried *E. acervulina* sporozoites and merozoites by immunofluorescence (IFA) using established procedures. Danforth and Augustine, Poult. Sci. 62 (11):2145-2151 (1983). Positive cultures were subcloned by limiting dilution and tested for the production a single Ig class by enzyme-linked immunosorbent assay. Wakefield et al., Clinica Chemica Acta 123:303-310 (1982).

Fusion of spleen cells from mice hyperimmune to *E. acervulina* sporozoites with myeloma cells resulted in the production of a hybridoma which secreted IgG$_{2a}$. Although no surface staining was observed, the McAb, designated S$_{11}$P$_1$A$_{12}$, appears to recognize an $^{125}$I- labeled 22 kDa surface protein as revealed by immunoblotting. Subsequent experiments have shown that this 22 kDa antigen, called p22, is present on the parasite surface as well as on the refractile body (RB) membrane. Although $S_{11}P_1A_{12}$ is not species-specific, since it cross-reacts with *E. tenella* sporozoites, it is developmental stage-specific since no recognition of *E. acervulina* merozoites was observed.

Recombinant phages prepared as described in Example 4 above were screened with these monoclonal antibodies using the procedure described in Example 5(B) above. One positive bacteriophage was identified, which was designated MA1. This bacteriophage was subcloned as described in Example 6 above, and transferred into *E. coli* Y1089 and a fusion protein produced therefrom as described in Example 6 above. The fusion protein was then purified as described in Example 8 above and screened with T cells from *E. acervulina* infected chickens as described in Example 9 above. The response at two different dose levels of MA1 was 4–5 times greater ($P<0.05$) than the activation induced by similar amounts of protein derived from identical fractions isolated from γgt11 homogenate.

EXAMPLE 16

Characterization of the MA1 Antigen

The expressed β-galactosidase fusion protein of MA1 was probed by immunoblotting with $S_{11}P_1A_{12}$ supernatant and appears to be about 125 kDa. This Mr estimate was corroborated by immunoblotting of MA1 with McAb to β-galactosidase.

The MA1 clone was subcloned into pUC-8 and used to transform *E. coli* JM83, as described in Example 10 above, to facilitate determining the molecular organization and DNA sequence thereof.

Digestion of pMA1 with EcoRI and subsequent agarose electrophoresis of the products revealed a DNA insert of about 200 bp in length. The molecular organization and expression of genes encoding the p22 antigen were examined by hybridization of $^{32}$P-labeled MA1 insert DNA to Southern blots of restriction enzyme-digested *E. acervulina* sporozoite DNA and Northern blots of RNA from both the sporozoite and merozoite stages. The p22 gene appears to exist as a single copy or low copy number sequence since only one hybridization band was observed with EcoRI (31 kbp), DraI (2.4 kbp), or HindIII (12 kbp) cut sporozoite DNA. Consistent with our immunological data that there is exclusive expression of the p22 antigen on sporozoites, labeled insert DNA hybridized only to sporozoite RNA and not to RNA from merozoites. One major hybridization band at 500 bp was observed which is in the range of predicted size of the mRNA (approximately 600 bp) based on the size of the p22 protein.

EXAMPLE 17

DNA Sequencing of MA1

The DNA sequence of the cDNA insert MA1 was determined using the dideoxy chain termination technique. Sanger, F. et al., Proc. Nat. Acad. Sci. U.S.A. 74:5463 (1977). Purified cDNA insert was obtained in accordance with Example 10 above, ligated to EcoRI digested M13mp18 DNA (BRL), and used to transfect JM101 cells. See Messing, J., Methods Enzymol. 101:20 (1983). Recombinant M13 clones (white plaque-colonies on Luria broth containing X-gal and IPTG) were picked and used to generate single stranded viral DNA. See Messing, supra. Sequencing reactions were performed as described by Williams et al., BioTechniques 4(2):138 (1986), with minor alterations using 30 μCi $^{35}$S-dATP (NEN 500 Ci/mMole) and analyzed on a 6% polyacrylamide sequencing gel. The complete sequence of M13 recombinant viral DNA and its complement representing both strands of the cDNA was ascertained and analyzed using the Intellegenetics DNA sequencing program. See generally T. Friedman, *Intellegenetics: A Short Course in Molecular Biology Software* Intellegenetics, Inc., Mountain View, Calif. (1985). The sequence of cDNA clone MA1, as determined by these procedures, is shown in Table I below.

TABLE I

DNA Sequence and Predicted Amino Acid Sequence of cDNA Clone MA1

```
                                                              45
GTA GTC GTC GTC GTC GTC GTG GGA AGT TCG ATG CAC GTC GTG GAA
VAL VAL VAL VAL VAL VAL VAL GLY SER SER MET HIS VAL VAL GLU

90
GTT CGG TCG TTC GGA GTC CGA AGA AGA CCA TCT ACA GAA TCA CGA
VAL ARG SER PHE GLY VAL ARG ARG ARG PRO SER THR GLU SER ARG

135
AGA AGT TCT CCT CTG ACT CTG TCT CCC TGC CTC TAT TCT GTT TTC
ARG SER SER PRO LEU THR LEU SER PRO CYS LEU TYR SER VAL PHE

180
CTC TGT CTA CTC CCC CCT GTC TCT GTA AGT TTC TGC CTT AAA AGG C
LEU CYS LEU LEU PRO PRO VAL SER VAL SER PHE CYS LEU LYS ARG
```

DNA sequencing of the pMA1 insert revealed a large open reading frame in one of the two possible sequence orientations. The other four reading frames are not considered since cloning into the EcoRI site of the lacZ gene of γ DNA does not destroy the reading frame, but is designed to encode a viable β-galactosidase fusion protein. Quite unexpected was the finding that no stop codon or long poly A tail was present in the sequence suggesting that we have cloned an internal region of the gene encoding the Mr22 protein. Consistent with the hybridization results and previous mapping studies no EcoRI, DraI, or HindIII sites occur within the sequence.

EXAMPLE 18

DNA Sequencing of cMZ-8

The DNA 5' portion and the 3' portion of the sequence of the cDNA insert cMZ-8 was determined using the procedures described in Example 17 above. This sequence is shown in Table II below. The bracketing identifies 14 tandem repeats of 7 amino acids each, together with a 15th repeat which is identical to the others except for differences at the 5th and 7th amino acids.

Probing Northern blots of *E. acervulina* sporozoite and merozoite RNA with $^{32}$P-labeled MC17 insert cDNA has shown hybridization only to nucleic acid derived

TABLE II

| DNA Sequence and Predicted Amino Acid Sequence of cDNA Clone cMZ-8 | |
|---|---|
| 5' CCTTTGCCCTTTTCTCCTCCTTCTACACCGGTCTCTCCTCCTTCTACACCGGTC | |
| P L P F [S P P S T P V] [S P P S T P V] | 18 |
| 55 TCTCCTCCTTCTACACCGGTCTCTCCTCCTTCTACACCAGTCTCTCCTCCTTCTACACCGGTT | |
| [S P P S T P V] [S P P S T P V] [S P P S T P V] | 39 |
| 118 TCGCCTCCTTCTACACCGGTCTCGCCTCCTTCTACACCGGTCTCGCCTCCTTCTACGCCGGTC | |
| [S P P S T P V] [S P P S T P V] [S P P S T P V] | 60 |
| 181 TCGCCTCCTTCTACACCGGTCTCGCCTCCTTCTACACCGGTCTCGCCACCTTCTACACCGGTC | |
| [S P P S T P V] [S P P S T P V] [S P P S T P V] | 81 |
| 244 TCGCCTCCTTCTACACCGGTTTCACCACCTTCTACACCGGTCTCACCACCTTCTACACCGGTT | |
| [S P P S T P V] [S P P S T P V] [S P P S T P V] | 102 |
| 307 TCGCCTCCTTCCTCTCCTGCGCCTGGTGCGGTTGGGGGGGTCAATTCAAGTCTGTCGCAACGC | |
| [S P P S S P A] P G A V G G T N S S L S Q R | 123 |
| 370 TCAACCTCCGAGCACTGGCACGCGTCAGTTTCCGTGCAGTTTGAGCGCTGGCGAGATCGCACG | |
| S T S E H W H A S V S V Q F E R W R D R T | 144 |
| 433 CCTGCCTCTGGGCTACGATTCGCTCCACTCGCCGAAGGGTGGCAATTCTGACTGCCGCAAGT | |
| P A S G L R F A P L A E G W A I L T A A S | 165 |
| 496 TGTAACCTCCACAACATCAGGCAGCGCCCAGGCTCCTCTGCTGCAGACCGTCGGCATTGCACT | |
| C N L H N I R Q R P G S S A A D R R H C T | 186 |
| 559 CGCTCCACTCGCTCCAGTCGCCGCATGTCGAGACGTCATCGTCACAAGGGCGGACTTCGTGGG | |
| R S H T R S S R R M S R R H R H K G G L R G | 207 |
| 622 TTTGTTTCACGATGCCGTCGGAGCGGATGCTGCAGGTTCTCTTCATTTGCTTCTCCGACGATT | |
| F V S R C R R S G C C R F S S F A S P T I | 228 |
| 685 CGCTCCAAGCTTACAGGTTACGGTGTCGCTGACGTCGGCTGTGGAGTACTCTTCGTACTCCGT | |
| R S K L T G Y G V A D V G C G V L F V L R | 249 |
| 748 CACACCGCACGCCGTATCCTCGCGCGTTCGTAGCGTCTTACTGCCAGAGCGGATTGTGCG | |
| H T A R R I L A R S . | 3' |

EXAMPLE 19

Characterization and DNA Sequencing of cDNA Clone MC17

The cDNA clone MC17 was identified and sequenced through use of essentially the same procedures as described above.

MC17 is a 130 kDa β-galactosidase fusion protein which was identified by immunoscreening an *Eimeria acervulina* sporozoite cDNA library with a monoclonal antibody designated S$_{16}$P$_3$A$_1$. MC17 represents a portion of a 58 kDa *E. acervulina* merozoite surface protein as determined by immunoblotting of extracts of $^{125}$I-labeled merozoites with S$_{16}$P$_3$A$_1$. This McAb, S$_{16}$P$_3$A$_1$, was prepared using the same procedures as described in Example 15 above. It is of the IgG$_1$ subclass and recognizes only *E. acervulina* merozoites and not sporozoites.

from the latter developmental stage. Hybridization of this probe to Southern blots of restriction enzyme-digested *E. acervulina* sporozoite and merozoite DNA suggests that MC17 cDNA may be interrupted by an intron in the genomic sequence. This conclusion is based on the observation that more than one hybridization band was observed with DraI (14.0 kbp and 2.0 kbp) and EcoRI (23 kbp and 7.6 kbp) digested DNA and neither restriction enzyme site is present in the cDNA sequence. In contrast, probing of BamHI *E. acervulina* DNA produced only one hybridization band (21 kbp) which may reflect the absence of this restriction site on the proposed intron.

The DNA sequence of MC17 is shown in Table III below.

TABLE III

| DNA Sequence and Predicted Amino Acid Sequence of cDNA Clone MC17 |
|---|
| 45 |
| GTA CGT CGT AGC GGC GCC CCG GCG GGG GTC GTC GCG TCG TCG GCA |
| HIS ALA ALA SER PRO ARG GLY ARG PRO GLN GLN ARG SER SER ARG |
| |
| 90 |
| GTG CCC CGA CTC CCA GGT CTG TGA TGA CCT CCC CTT CGA CGA CGA |
| HIS GLY ALA GLU GLY PRO ASP THR THR GLY GLY GLU ALA ALA ALA |
| |
| 135 |
| GTT CAA CCT CCT CCT GCT GCA GGC CTT CTA CAC CTA GGC ACC CCC |
| GLN VAL PRO PRO PRO ALA ALA GLY LEU LEU HIS LEU GLY THR PRO |
| |
| 180 |
| TGT TGG TGC TTA CGT TTG CGG TTG ACG ACA ACA ACC CCC GAA ACG |
| THR THR THR ASN ALA ASN ALA ASN CYS CYS CYS TRP GLY LEU CYS |
| |
| 225 |
| AAC CTG ACG GAA GTT TGT GTT AAC TTT ATA CAC GAA CAC GTT TTT |
| LEU ASP CYS LEU GLN THR GLN LEU LYS TYR VAL LEU VAL GLN |
| |
| 238 |
| TTT TTT TTT TTT C |

The DNA sequence of the MC17 insert revealed a long poly A tail suggesting that we have cloned the 3'-end of the cDNA. The sequence also appears to be composed of several amphipathic alpha helices which have been associated with T lymphocyte recognition sites. Consistent with this finding is the significant in vitro activation of T lymphocytes obtained from *E. acervulina*-immune chickens by the β-galactosidase fusion protein coded for by cMZ-8.

EXAMPLE 20

Characterization of cDNA Clone MA16

MA16 is a 140 kDa β-galactosidase fusion protein which was identified by immunoscreening and an *E. acervulina* merozoite cDNA library with an IgM subclass monoclonal antibody designated 12-07. This monoclonal antibody was prepared using essentially the same procedures as described in Example 15 above. MA16 represents a portion of a p58/p70 *E. acervulina* merozoite surface protein as revealed by the immunoblotting of extracts of $^{125}$I-labeled merozoites with 12-07. This McAb cross-reacts with *E. acervulina* sporozoite surface antigens which are similar in size to the merozoite constituents as revealed by immunoblotting of labeled sporozoites. The surface locale of the p58/p70 antigen has been corroborated by immunofluorescence staining of *E. acervulina* sporozoites and merozoites with McAb 12-07. The relationship of p58 and p70 to each other is unknown.

EXAMPLE 21

Screening of Fusion Proteins With Immune Sera From *E. acervulina* Infected Chickens An aliquot of the each fusion protein preparation (cMZ-8, cSZ-1, MA1, MC17, MA16) was separated on the basis of molecular weight by SDS-polyacrylamide gel electrophoresis (SDS-PAGE) and transblotted to nitrocellulose paper. The Western blots were probed either with monoclonal antibodies specific for the fusion protein or for β-galactosidase or with immune sera from *E. acervulina*-infected chickens. The binding of first Ab was detected with biotinylated-anti-Ig followed by avidin-peroxidase and developed with 0.5 mg/ml 4-chloro-1-napthol, 0.01% $H_2O_2$.

Of these five fusion proteins, only cMZ-8 was recognized by immune sera taken from *E. acervulina* infected chickens.

EXAMPLE 22

Vaccine Trial Results Recombinant MA1 and MA16 Eimeria Antigens

One-day-old chickens (10 birds/group) were immunized by subcutaneous injection of MA1 (1.0 μg/bird) or MA16 (0.1 μg/bird) emulsified in Complete Freund's adjuvant. Seven days later, the MA1-immunized chickens were given a booster immunization. MA16-Immunized chickens did not receive a booster immunization. Two weeks later immunized and unimmunized control chickens were challenged with an oral dose of 200,000 oocysts of live *E. acervulina* coccidia. Treatments of the various groups are summarized in Table IV below. Six days post-coccidial challenge, all chickens (including a control group which was not immunized or challenged) were killed and examined for lesion score, weight gains (over starting weights), pigment levels in serum and feed conversion ratios. The results are reported in Table V below.

TABLE IV

| | Immunization and Challenge Treatments | | | |
|---|---|---|---|---|
| Group | Antigen | Dose, μg | Boost | Challenge |
| 1 | — | — | — | — |
| 2 | — | — | — | + |
| 11 | MA1 | 1.0 | + | + |
| 13 | MA16 | 0.1 | — | + |

TABLE V

| | Responses to Treatments | | | |
|---|---|---|---|---|
| Group | Average weight gain (g) | Lesion score | Pigment (mg/ml of serum) | Feed conversion (wt. feed/wt. gain) |
| 1 | 305 | 0 | 1.1 | 1.69 |
| 2 | 251 | 2.2 | 0.4 | 2.37 |
| 11 | 333$^a$ | 1.0$^b$ | 0.6 | 1.99$^d$ |
| 13 | 311$^a$ | 2.2 | 1.1$^c$ | 1.99$^d$ |

$^{a,c}$Significantly (P < 0.05) greater than group 2;
$^{b,d}$Significantly (P < 0.05) less than group 2.

EXAMPLE 23

Vaccine Trial Results Recombinant MA1 and Polyvalent Recombinant Eimeria Antigens One-day-old chickens (15 per group were immunized by subcutaneous injection of MA1 (1.0 μg/bird) or a combination of MA1 (1.0 μg/bird), cMZ-8 (1.0 μg/bird), and MA16 (0.1 μg/bird) emulsified in Complete Freund's adjuvant. Seven days later, the chickens immunized with the combined antigen preparation were inoculated with 200 *Eimeria acervulina* oocysts to serve as a natural boost to the immune response. This inoculation dose does not have any measurable effect on weight, feed conversion, lesion score, or pigment parameters. Two weeks later the immunized and control chickens were challenged with an oral dose of 200,000 oocysts of live *Eimeria acervulina* coccidia. Six days post-coccidial challenge, all chickens were killed and examined for lesion score, weight gains, and pigment levels in the serum. The results of those groups exhibiting a significant level of protection compared to controls are shown below in Table VI.

TABLE VI

| Group | Antigen | Dose | Oocyst boost | Challenge | Pigment (mg/ml of serum) | Average weight gain (g) | Feed conversion (wt. feed/wt. gain) |
|---|---|---|---|---|---|---|---|
| 1 | — | — | — | — | 6.0 | 338.8 | 1.76 |
| 2 | — | — | — | + | 1.7 | 277.1 | 2.04 |
| 9 | combo | 2.1 μg | + | + | 2.9$^a$ | 301.3 | 1.93$^b$ |
| 11 | MA-1 | 1.0 μg | — | + | 1.9 | 331.0$^c$ | 1.89$^b$ |

$^a$Serum pigment values for this group were significantly greater (P < 0.05) than for infected control group 2.
$^b$Feed conversions were significantly (P < 0.05) less than for infected group 2.
$^c$Weight gain for this group were significantly greater (P < 0.05) than for infected control group 2.

The foregoing examples have been provided to illustrate the present invention. They are not to be taken as limiting thereof, the scope of the invention being defined by the following claims. Equivalents of the claims are to be included therein.

We claim:

1. A recombinant DNA sequence encoding the *Eimeria acervulina* antigen derived from clone cMZ-8, MA1, MC17, cSZ-1, or MA16 or degenerate DNA sequences encoding said antigens.

2. A DNA sequence as described in claim 1, wherein said sequence is derived from clone cMZ-8.

3. A DNA sequence as described in claim 1, wherein said sequence is derived from clone MA1.

4. A DNA sequence as described in claim 1, wherein said sequence is derived from clone MC17.

5. A DNA sequence as described in claim 1, wherein said sequence is derived from clone cSZ-1.

6. A DNA sequence as described in claim 1, wherein said sequence is derived from clone MA16.

7. A vector comprising a DNA sequence of claim 1 operatively linked to expression regulatory elements capable of inducing the expression of said antigen in a transformed host cell.

8. A bacterial host cell transformed with the vector of claim 7.

* * * * *